United States Patent [19]

von Zeppelin

[11] Patent Number: 5,074,870
[45] Date of Patent: Dec. 24, 1991

[54] CLAMP FOR CLAMPING BLOOD VESSELS OR ANEURYSMS

[76] Inventor: Dieter von Zeppelin, D-8023 Pullach, Fed. Rep. of Germany

[21] Appl. No.: 591,716

[22] Filed: Oct. 2, 1990

[30] Foreign Application Priority Data

Oct. 7, 1989 [DE] Fed. Rep. of Germany ... 8911948[U]

[51] Int. Cl.$^5$ .............................................. A61B 17/00
[52] U.S. Cl. .................................... 606/158; 606/157; 606/151
[58] Field of Search ......................... 606/151, 157, 158

[56] References Cited

U.S. PATENT DOCUMENTS

| | | | |
|---|---|---|---|
| 4,765,335 | 8/1988 | Schmidt et al. | 606/158 |
| 4,932,955 | 6/1990 | Merz et al. | 606/158 |
| 4,943,298 | 7/1990 | Fujita et al. | 606/151 |

*Primary Examiner*—Stephen C. Pellegrino
*Assistant Examiner*—Gary Jackson
*Attorney, Agent, or Firm*—Eric Y. Munson; Mark P. Stone

[57] ABSTRACT

A clamp for clamping blood vessels or aneurysms has a pair of operational arms and a corresponding pair of hemostatic ends for engaging a blood vessel or aneurysm. The operating arms are attached to each other, without pivot mounting, with a coil spring having at least one winding, by fixedly connecting each end of the coil spring to a different one of the operational arms. The coil spring biases the clamp so that the hemostatic ends of the clamp are opened when the operating arms of the clamp are moved apart from each other. In this manner, visual obstruction of the hemostatic ends of the clamp is significantly reduced during a clamping procedure, and the cost of manufacture of the clamp is reduced by elimination of pivot mounting of the clamp arms.

2 Claims, 1 Drawing Sheet

CLAMP FOR CLAMPING BLOOD VESSELS OR ANEURYSMS

BACKGROUND OF THE INVENTION

The present invention pertains to surfical procedures in which a blood vessel or aneurysm must be blocked by pinching off the vessel with a device, either temporarily or permanently, to prevent bleeding or hemorrhaging.

In surgery, and in particular microsurgery techniques, blood vessels, aneurysms and the like, often must be clamped to prevent bleeding and hemorrhaging in very narrow special surroundings. The problem is a particularly burdensome one when clamping deep-lying, craneal aneurysms due to the fact that space and visibility is severely limited by surrounding brain tissue.

Clamps utilized for clamping blood vessels and aneurysms have heretofore generally had a configuration in which the clamp or an end of the clamp is grasped by forceps and squeezed to open the hemostatic end of the clamp for application to a blood vessel. The handling of the clamp by forceps from outside partially conceals the clamp and positions the forceps to substantially obstruct visibility of the clamp and the blood vessel or aneurysm to which the clamp is being applied.

With a clamp configuration in which the clamp is operated by squeezing a portion of the clamp with a pair of forceps, to assure the clamp is not dropped during application, particularly with difficult reaches, the forceps used for applying the clamp generally must have a shaped end portion which captures the clamp. Some designs have even used interlocking means such as a pin which is formed at the tip of the forceps which fits in a corresponding hole formed in the portion of the clamp wherein the clamp is held thereby. This requires the ends of the forceps used for application to be enlarged which further obstructs visibility of the area in which the clamp is being utilized.

Blood vessel and aneurysm clamps have been constructed in two general configurations. In the first the arms of the clamp are pivotally attached to one another at a central location and do not cross over one another so that when the operational end of the clamp is squeezed together the hemostatic end of the clamp opens. The second type of clamp is a one piece construction of spring steel in which the hemostatic ends of the clamp cross over one another so that as the spring expands outwardly the hemostatic ends are closed together. This type of clamp is operated by squeezing the spring portion to open the hemostatic ends. In both of these clamp types the forceps used for application must engage the clamp from outside thereby resulting in the visible obstruction as discussed above.

DE 37 23 167 A1 discloses a clamp for pinching off a blood vessel or aneurysm which is operated by spreading out the operational ends thereof to open hemostatic ends of the clamp for application. It is possible to grasp the clamp with an application instrument from within the operational ends of the clamp, thereby substantially reducing visual obstruction in the area in which the clamp is utilized. Visual effectiveness is improved since the application instrument engages the clamp from within its structure, rather than grasping the clamp from outside, thus reducing the size of the clamp and instrument combination. Furthermore, this construction substantially improve visibility of the hemostatic portion of the clamp at the vessel or aneurysm during application. But this clamp consists of a pair of arms being manufactured of solid material and being assembled by a pin to provide pivotal movement therebetween. The manufacture of this known clamp is costly, especially because of the accuracy of fit being necessary for the pivotal bearing.

There exists a need for a blood vessel or aneurysm clamp being of simple design which can be easily manufactured.

SUMMARY OF THE INVENTION

The invention provides a clamp of the type mentioned, the arms thereof cross each other without being pivot-mounted whereby the means for biasing said arms is a coil spring having at least one winding and each of the ends of said coil spring being connected fixedly to one of said operational ends of said arms.

The clamp according to the invention does not need a pivot-mounted bearing so that it can be manufactured easily with low costs.

The ends of said coil spring may cross each other within the area between the winding of the coil spring and the connecting points of the coil spring at the ends of the arms.

The clamp according to the invention is visible in nearly its full extend during application. Furthermore, the hemostatic ends of said arms open with their full length.

In the following the invention is explained in detail in connection with the drawings.

DESCRIPTION OF THE BEST MODES FOR CARRYING OUT THE INVENTION

Figure 1:
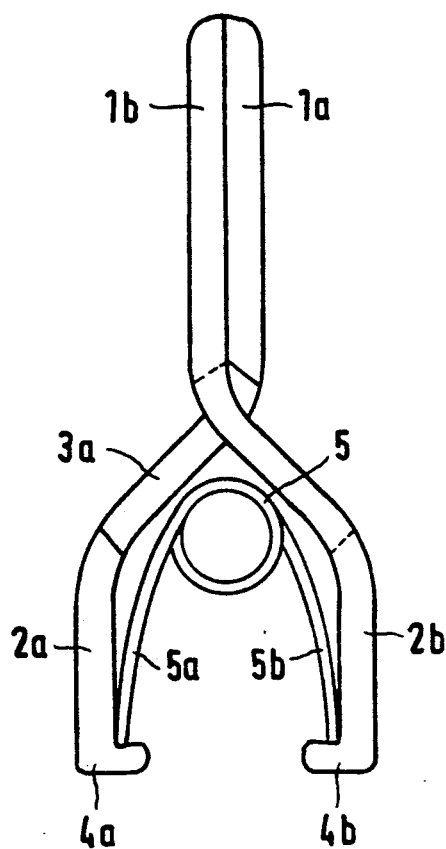
FIG. 1 is a side view of a blood vessel or aneurysm clamp according to a first embodiment of the invention as described herein.
Figure 2:
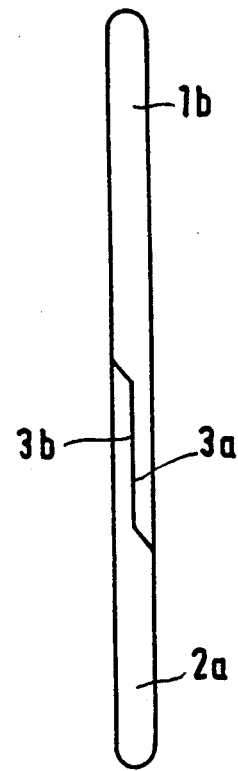
FIG. 2 is a top view of the blood vessel or aneurysm clamp shown in FIG. 1.

As shown in FIGS. 1 and 2 the clamp consists of two arms each having a hemostatic end $1a$, $1b$ and an operational end $2a$, $2b$. Said arms cross each other. They are manufactured especially of wire material which can be bent in a corresponding form. Within the cross over area $3a$, $3b$ the arms have depressions so that the hemostatic ends $1a$, $1b$ are placed one above the other.

Between the operational ends $2a$, $2b$ there is located the spring 5 urging the hemostatic ends against each other. Said spring 5 is in the form of a coil spring having at least one winding the ends $5a$, $5b$ of which are fixed at the inner sides of the operational ends $2a$, $2b$.

The free extremities $4a$, $4b$ of the operational ends $2a$, $2b$ are provided with engaging elements for an applying instruments not shown by means of which the hemostatic ends $1a$, $1b$ of the clamp can be opened by expanding the operating ends $2a$, $2b$ of the arms. By this opening movement the two arms of the clamp are pivoted about the middle axis of the coil spring 5.

The free ends of the engaging elements $4a$, $4b$ can be formed half spherically, cylindrically, conically or they may have a similar form. The engaging elements also may be pyramid-shaped so that it is possible to fix the clamp at different angles with respect to the applying instrument. Thereby it is not necessary to manufacture many models of the clamp.

The coil spring is biased such that the operational ends 2a, 2b are pulled together and the hemostatic ends 1a, 1b are pressed against each other with a predetermined force.

In order to apply the clamp an usual applying instrument is introduced between the operational ends 2a, 2b. The applying instrument has recesses corresponding to the projections of the operational ends of the clamp into which the projections can engage.

Since the applying instrument grasps the operational ends of the clamp from the inside and not from outside, there is substantially reduced visual obstruction when applying a clamp as no parts of the clamp are covered.

Figure 3:
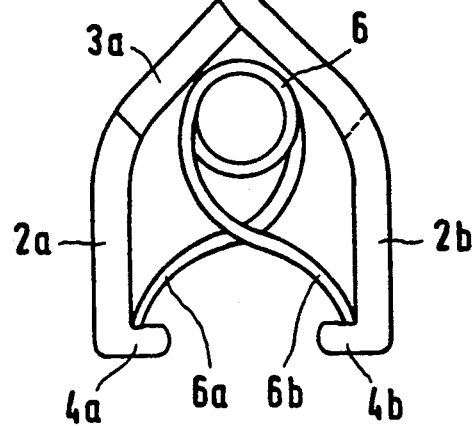
FIG. 3 is a side view of a blood vessel or aneurysm clamp according to a second embodiment of the invention.

FIG. 3 shows a modified embodiment of the invention wherein the ends 6a, 6b of the coil spring 6 cross over between the operational ends 2a, 2b. Hereby, an increased force may be applied to the operational ends 2a, 2b.

I claim:

1. A clamp for clamping blood vessels or aneurysms to cease blood flow therefrom comprising a pair of arms each having a hemostatic end and an operational end, said arms having a mirror image configuration and being mounted one to the other such that said arms cross each other so the hemostatic ends of said arms align with and oppose one another, said hemostatic ends opening relative to one another when said operational ends are similarly opened, and means for biasing said arms to apply clamping force between said hemostatic ends of said arms, said operational ends of said arms having engaging means for securing said operating ends to an application instrument so said clamp is held by said instrument, the clamp being operated by spreading the operational ends of said clamp arms to open said hemostatic ends for application of said clamp to a blood vessel or aneurysm, and then released to provide clamping force thereto, characterized in that said clamp arms cross each other without being pivot-mounted, that said means for biasing said arms is a coil spring having at least one winding, each of the ends of said coil spring being connected fixedly to one of said operational ends of said arms.

2. A clamp according to claim 1, characterized in that the ends of the coil spring cross each other within the area between the winding of the coil spring and the extremities of the operational ends of said arms.

* * * * *